(12) United States Patent
Delmas et al.

(10) Patent No.: US 9,388,207 B2
(45) Date of Patent: Jul. 12, 2016

(54) PROCESS FOR THE SEPARATION OF LIGNINS AND SUGARS FROM AN EXTRACTION LIQUOR

(75) Inventors: Michel Delmas, Auzeville-Tolosane (FR); Bouchra Benjelloun Mlayah, Pompertuzat (FR)

(73) Assignee: COMPAGNIE INDUSTRIELLE DE LA MATIERE VEGETABLE—CIMV, Levallois Perret (FR)

( * ) Notice: Subject to any disclaimer, the term of this patent is extended or adjusted under 35 U.S.C. 154(b) by 0 days.

(21) Appl. No.: 13/700,287

(22) PCT Filed: Jun. 1, 2011

(86) PCT No.: PCT/EP2011/059020
§ 371 (c)(1),
(2), (4) Date: Nov. 27, 2012

(87) PCT Pub. No.: WO2011/154293
PCT Pub. Date: Dec. 15, 2011

(65) Prior Publication Data
US 2013/0085269 A1    Apr. 4, 2013

(30) Foreign Application Priority Data
Jun. 8, 2010    (FR) ...................................... 10 54478

(51) Int. Cl.
*C07G 1/00*    (2011.01)
*C07H 1/00*    (2006.01)
(Continued)

(52) U.S. Cl.
CPC .. *C07H 1/00* (2013.01); *C07H 1/06* (2013.01); *C08B 37/0003* (2013.01); *C08H 6/00* (2013.01)

(58) Field of Classification Search
CPC .................................... C07G 1/00; C08H 6/00
USPC ......................................................... 530/500
See application file for complete search history.

(56) References Cited

U.S. PATENT DOCUMENTS

| | | | | |
|---|---|---|---|---|
| 1,958,624 A | * | 5/1934 | Howard et al. | 530/500 |
| 2,380,448 A | * | 7/1945 | Katzen | 530/507 |

(Continued)

FOREIGN PATENT DOCUMENTS

| | | |
|---|---|---|
| EP | 1 180 171 B1 | 2/2002 |
| EP | 1 686 138 A1 | 8/2006 |
| FR | 2 868 336 A1 | 10/2005 |

OTHER PUBLICATIONS

Thring, R. W., "Recovery of a solvolytic lignin: Effects of spent liquor/acid volume ratio, acid concentration and temperature,". Biomass, 1990, 23, 289-305 (Abstract).*

(Continued)

*Primary Examiner* — Liam J Heincer
*Assistant Examiner* — Nicholas Hill
(74) *Attorney, Agent, or Firm* — Young & Thompson

(57) ABSTRACT

A process for the separation of lignins and sugars from an extracted liquor, including, in the form of dry matter (DM), lignins and sugars, includes: a) concentrating the extracted liquor, in order to obtain a liquor having dry matter in a proportion of between 60 and 70%; b) mixing the concentrated liquor with water in equal parts by weight; c) stirring the mixture in order to disperse the lignins and to obtain a stable suspending of the lignins; d) filtering the solution, wherein the mixing is carried out by introducing the concentrated liquor into the water; and the temperature of the solution, during the suspending, is between 50° C. and 60° C.

13 Claims, 1 Drawing Sheet

(51) Int. Cl.
*C08B 37/00* (2006.01)
*C08H 7/00* (2011.01)
*C07H 1/06* (2006.01)

(56) References Cited

U.S. PATENT DOCUMENTS

| | | | |
|---|---|---|---|
| 4,764,596 A * | 8/1988 | Lora et al. | 530/507 |
| 7,402,224 B1 | 7/2008 | Avignon et al. | |
| 2007/0083039 A1 * | 4/2007 | Hayashi et al. | 530/502 |

OTHER PUBLICATIONS

Merriam-Webster, website. Definition of the word "stir," Feb. 2, 2014.*

Chase, G. C., et al., "Filtration," in Kirk-Othmer Encyclopedia of Chemical Technology, 2003, 77 pages.*

International Search Report, dated Aug. 5, 2011, from corresponding PCT application.

* cited by examiner

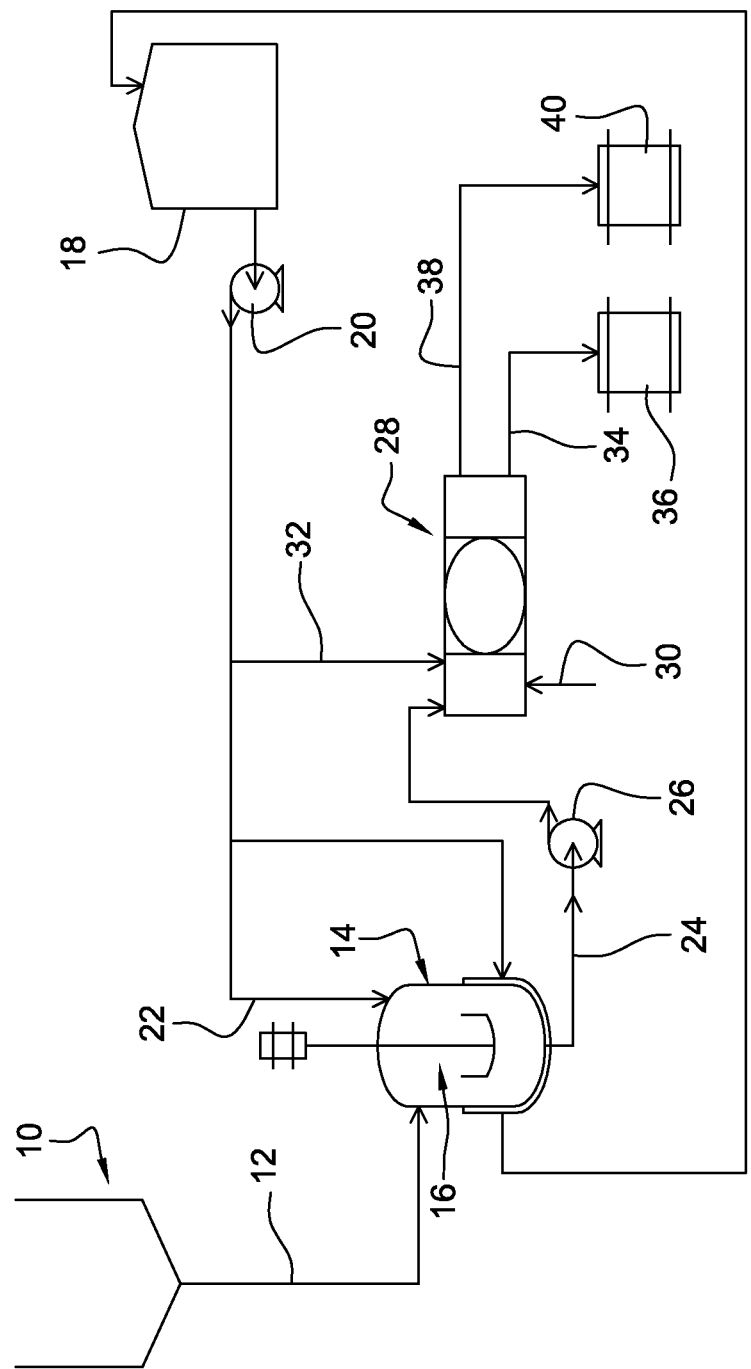

PROCESS FOR THE SEPARATION OF LIGNINS AND SUGARS FROM AN EXTRACTION LIQUOR

TECHNICAL FIELD OF THE INVENTION

The invention relates to a process for the separation of lignins and sugars from an extraction liquor, said extracted liquor comprising lignins and sugars in the form of dry matter.

TECHNOLOGICAL BACKGROUND

The invention relates in particular but without implied limitation to the separation of lignins and sugars in an extracted liquor which is obtained from a process for the production of paper pulp, lignins, sugars and acetic acid and which is described in European Patent EP-B1-1 180 171 (or U.S. Pat. No. 7,402,224).

Such a process, among other extraction processes, in particular starting from a lignocellulose starting material, makes it possible to obtain, in addition to a solid fraction constituting the paper pulp of the organic phase, an organic phase comprising in particular, in solution, monomeric and polymeric sugars and lignins resulting from the initial plant starting material.

In the context of the recovery in value of all the products obtained by such a process, it is important to be able to separate the lignins from the sugars as completely as possible, without denaturing the quality of the lignins.

This is also done in order to avoid obtaining, according to various known techniques, a "pulp" formed of lignins which exist when lignin "grains" are "stuck together by" sugars.

The various known processes make it possible in particular to industrially obtain degraded and sulphur-comprising lignins (the presence of sulphur being due to the production process).

"Kraft" lignins are concerned in particular.

Another process known from the document EP-1 686 138 provides a process for the separation and recovery of an acid/sugar liquid phase from a lignocellulose starting material. However, this process does not make it possible to separate the lignins and thus not without degrading them, since, in this process, the lignins are agglomerated to give a "lignophenol derivative" product obtained during the process by impregnation of the starting material using a "phenol derivative".

The present invention is targeted at providing a separation process, in particular one which is highly effective in an acidic medium, which avoids any phenomenon of agglomeration of the lignin particles, that is to say which prevents the formation of aggregates composed of lignins and sugars.

BRIEF SUMMARY OF THE INVENTION

With this aim, the invention provides a process for the separation of lignins and sugars from an extraction liquor, referred to as extracted liquor, comprising, in the form of dry matter, lignins and sugars, characterized in that it consists in:

a) concentrating the extracted liquor, in particular by evaporation, in order to obtain a concentrated liquor comprising dry matter in a proportion of between 60 and 70% by weight;

b) producing a solution by mixing the concentrated liquor with water in equal parts by weight;

c) stirring the mixture in order to produce a dispersion of the lignins in the mixture and to obtain a stable suspending of the lignins in the solution;

d) filtering the solution comprising the suspended lignins, in particular using a filter press, for the purpose of separating the lignins in suspension in the solution, in which process:

the mixing is carried out by introducing the concentrated liquor into the water;

the temperature of the solution, during the suspending, is between 50° C. and 60° C.

Thus, according to the invention, the separation of the lignins and sugars is based on the hydrophobic property of the lignin.

Before the separation proper by filtration, a stable suspending of the lignins in an aqueous medium is thus carried out.

Furthermore, the stable suspending makes it possible to avoid all the phenomena of clumps and blockage or obstruction in the various flowing streams and also in the filtration membranes.

The suspending according to the invention, prior to the filtration, makes it possible to separate individual particles of lignins from the solution of sugars and to thus obtain optimum conditions for the filtration in this physical state of suspension.

According to other characteristics of the invention:

the stirring of the solution is carried out by rotating;

after the filtration stage d), the filtered material is dried in order to obtain the lignins as a powder, the size of the particles of which is between 20 and 50 microns;

the dry matter comprises, by weight, approximately 50% of lignins and approximately 50% of sugars and other products;

at 50° C., the viscosity of the solution is equal to approximately 0.26 Pa·s and the density of the solution is equal to approximately 1.074;

the suspension obtained in stage c) is stable, at ambient temperature, for at least two hours;

the extracted liquor is obtained from a process for the production of paper pulp, lignins, sugars and acetic acid which comprises the successive stages consisting (i) in bringing together annual or perennial plants, used in all or part, which constitute the initial lignocellulose starting material, and a formic acid mixture comprising at least 5% by weight of acetic acid which is brought to a reaction temperature of between 50° C. and 115° C.; and (ii) in subsequently separating, at atmospheric pressure, the solid fraction constituting the paper pulp from the organic phase, comprising in particular, in solution, the starting formic and acetic acids, dissolved monomeric and polymeric sugars, lignins and acetic acid resulting from the initial plant starting material; the process additionally comprising a preliminary stage consisting in carrying out a preimpregnation of the plant material at atmospheric pressure and at a temperature lower by at least 30° C. than the reaction temperature.

The operation in which the extracted liquor and the water are brought into contact, for the purpose of producing the dispersion, and the suspending are carried out at 55° C. plus or minus 5° C.

It is the temperature obtained after carrying out the mixing, it being possible for the concentrated extracted liquor, in particular after evaporation, to initially be at a higher temperature, for example of the order of 80° C.

The operation in which the concentrated extracted liquor is brought into contact with water is carried out, for example, in a vessel into which first the water is introduced and then into which the concentrated liquor is introduced with stirring by rotating, for example using a turbine, in order to obtain the dispersing and suspending effect.

Tests have shown that the suspension is stable, at ambient temperature, for at least two hours.

Different tests have also made it possible to observe that this stability is virtually independent of the temperature and thus that the cooling from the temperature of mixing with water down to ambient temperature has no impact on the stability.

After filtration, in particular in a filter press, a pressed cake of lignins is obtained, and also a filtrate referred to as sugar-comprising liquor.

In addition to the sugar-comprising liquor recovered directly by filtration, which corresponds to approximately three quarters of the total volume of the sugar-comprising liquor, approximately a quarter of the sugar-comprising liquor is subsequently recovered by washing the pressed cake of lignins.

After washing, the sugar content of the cake of lignins is less than 1%.

It is found that the physical and chemical characteristics of the lignins are in no way modified by the separation process according to the invention.

In particular, in the context of the process mentioned above according to Patent EP-B1-1 180 171, the lignins retain the physicochemical characteristics which they exhibit when they result from the process.

BRIEF DESCRIPTION OF THE FIGURE

The single FIGURE appended as an annex represents, diagrammatically, a plant for the implementation of the process according to the invention.

DETAILED DESCRIPTION OF THE FIGURE AND OF THE PROCESS

The FIGURE gives a diagrammatic representation of an evaporator 10 into which an extraction liquor or extracted liquor is introduced for the purpose of carrying out the concentrating thereof by evaporation.

The evaporation is, for example, carried out until a concentration of dry matter preferably of 65% by weight is obtained.

Subsequently, the concentrated liquor is introduced, by means of a pipe 12, into a vessel 14.

The vessel 14 is equipped with means 16 for stirring by rotating.

The product comprises a source 18 of water which is heated, for example, to approximately 50° C.

The heating of the water present in the stock or source 18 can, for example, be carried out by bringing the water into contact around the vessel 14 into which the hotter concentrated liquor and the water are introduced.

A pump 20 make it possible to circulate the water from the source 18, on the one hand, around the vessel and, on the other hand, makes it possible to introduce the water into the vessel 14 via the pipe 22.

In accordance with the invention, the concentrated liquor/water mixing is carried out by treatment of successive batches and it takes place by introducing first the water and then the concentrated liquor into the water.

On conclusion of the mixing and of the dispersing for the stable suspending of the lignins in the solution carried out in the vessel 14, the solution comprising the suspended lignins is extracted from the vessel via a pipe 24 and a pump 26.

This solution, comprising the lignins in stable suspension, is subsequently introduced into a filter press 28 for the purpose of separating the lignins in suspension in the solution.

The filter press comprises means 30 which can make it possible to introduce compressed air for blowing operations.

The filter press 28 is also connected to the water source 18 via a pipe 32 which makes possible the introduction, into the filter press, of water for washing the filtered and pressed cake of lignins.

The FIGURE also gives a diagrammatic representation of an outlet pipe 34 via which the sugar-comprising liquor 36 resulting from the pressing is recovered and a pipe 38 via which the aqueous wash liquor 40 from the filtered and pressed cake of lignins is recovered.

The total recovery of the sugar-comprising liquor results from the sum of the sugar-comprising liquor 36 obtained directly by pressing and of the sugar-comprising liquor present in the aqueous wash liquor 40.

The vessel 14 and its dispersing means 16 are, for example, supplied by PMS.

An example of equipment for stirring by rotating, also known as "Rotor/stator mixing device", from PMS (Pompes et Mélangeurs Michel Sarrazin) is described and represented in the document FR-B1-2 868 336.

Such a mixer, used for the tests described in detail below, makes it possible to carry out dispersing using a turbine, the rotational speed of which is between 10 000 and 15 000 revolutions per minute for a turbine perimeter of 20 millimeters for the equipment used in the laboratory, i.e. a correspondence, for a turbine perimeter of 140 millimeters for a pilot plant, of 1700 to 2100 revolutions per minute.

Under the conditions of implementation of the process according to the invention, the size of the lignin particles is between 20 and 50 microns and the stability of the suspension, always greater than at least two hours, was confirmed by the "Turbiscan" optical measurement method.

The filter press used, for example from Faure or Choquenet, is of the polypropylene membrane type comprising several plates which are filled with the suspension at a predetermined pressure, for example equal to 5 bar.

A washing stage is subsequently carried out, followed by a final compacting.

The washing makes it possible to recover the whole of the sugar-comprising liquors and to remove the residual acid from the lignin cake.

This washing can be carried out with water at approximately 50° C. or by combining air and water (washing/blowing).

For the various tests, the concentrated liquor/water ratio by weight is always equal to 1 and the temperature of the mixture is equal to approximately 50° C.

For the filtration, use is made, in a first step, of the following parameters:

filtration pressure: 5 bar washing pressure: 2.5 bar temperature: the aqueous wash liquor is sent to a temperature so as to "reheat" the cake and to carry out the washing at a temperature greater than 40° C.

washing up to a pH of approximately 4 the compacting is carried out at a pressure of 7 bar.

Examples of results for a suspension of lignins which result from a plant starting material composed of wheat straw are given in the following tables.

1. Suspending

| Test | Ext. liquor A (kg) | Ext. liq. T (° C.) | Ext. liq. DM (%) | Water A (kg) | Water T (° C.) | Stirring time (min) | Turbine speed (rev/min) |
|---|---|---|---|---|---|---|---|
| 1 | 100 | 80 | 55.94 | 100 | 50 | 5 | 1800 |
| 2 | 100 | 72 | 52.4 | 100 | 55 | 5 | 1800 |

2. Filtration

| Test | Dispersion A (kg) | Dispersion T (° C.) | Filter inlet T (° C.) | Filtration P (bar) | Filtration D (min) | Precompacting P (bar) |
|---|---|---|---|---|---|---|
| 1 | 72 | 58.8 | 51 | 5 | 15 | 5 |
| 2 | 100 | 55 | 46 | 5 | 50 | 5 |

3. Washing

Test 1

| Aqueous washing liquor A (kg) | Aqueous washing liquor T (° C.) | Washing P (bar) | Washing D (min) | Compacting P (bar) |
|---|---|---|---|---|
| 24 | 46 | 5 | 60 | 7 |

Test 2

| Aqueous washing liquor A (kg) | Aqueous washing liquor T (° C.) | Washing P (bar) | Unit washing D (min) | Blowing P (bar) | Unit blowing D (min) | Washing D (min) | Compacting P (bar) |
|---|---|---|---|---|---|---|---|
| 65.5 | 48-40 | 5 | 3 | 5 | B1 = 10 min, B2 to B8 = 7 min | 80 | 7 |

4. Material Balances

Test 1

| | Suspension | Sugar-comprising liquors | Lignins | Aqueous washing liquor |
|---|---|---|---|---|
| A (kg) | 72.0 | 58 | 19 | 24 |
| Acidity (%) | 19.68 | 27.87 | 2.96 | 2.00 |
| Acids (kg) | 14.18 | 16.17 | 0.56 | 0.48 |
| H$_2$O (kg) | 37.22 | 32.52 | 7.12 | 23.19 |
| DM (%) | 28.65 | 16.07 | 59.59 | 1.38 |
| DM (kg) | 20.64 | 9.32 | 11.32 | 0.33 |

Test 2

| | Suspension | Sugar-comprising liquors | Lignins | Aqueous washing liquor |
|---|---|---|---|---|
| A (kg) | 100.0 | 74 | 21 | 65.5 |
| Acidity (%) | 21.00 | 22.35 | 2.90 | 1.40 |
| Acids (kg) | 21.00 | 16.54 | 0.62 | 0.92 |
| H$_2$O (kg) | 53.23 | 48.59 | 7.52 | 60.53 |
| DM (%) | 25.77 | 11.98 | 61.21 | 2.65 |
| DM (kg) | 25.77 | 8.87 | 12.85 | 4.05 |

The invention can also be implemented in a solid/liquid mixer which operates continuously, for example by means of a "magic LAB®" device equipped with an "Ultra-Turrax®" single-stage dispersing module which are sold by IKA®-Werke GmbH & Co. KG, D-79219, Staufen, Germany.

The invention claimed is:

1. A process for the separation of lignins from an acidic paper pulp extraction liquor, the process comprising:
   (a) concentrating the extraction liquor by evaporation to obtain a concentrated liquor comprising dry matter in an amount of between 60% and 70% by weight, the dry matter comprising lignins and sugars;
   (b) mixing the concentrated liquor with water in equal parts by weight to dilute the liquor, wherein said mixing is carried out by introducing the concentrated liquor into the water;
   (c) stirring the mixture from step (b) and adjusting the temperature of the mixture to between 50° C. and 60° C. to disperse the lignins in the mixture and to obtain a stable suspension of the lignins in solution; and
   (d) filtering the suspension of lignins in solution from step (c) to remove the lignins.

2. The process according to claim 1, wherein said stirring the mixture of step (c) is carried out by rotating the mixture.

3. The process according to claim 1, further comprising drying the removed lignins to obtain lignin particles as a powder, the size of particles in the powder being between 20 and 50 microns.

4. The process according to claim 1, wherein the dry matter comprises approximately 50% by weight of lignins, and approximately 50% by weight of sugars and other products.

5. The process according to claim 1, wherein the suspension of the lignins in solution at 50° C. has a viscosity of approximately 0.26 Pa·s, and a density of approximately 1.074.

6. The process according to claim 1, wherein the suspension of the lignins in solution obtained in step (c) is stable, at ambient temperature, for at least two hours.

7. The process according to claim 1, wherein said extraction liquor is obtained from a paper pulp production process, said production process comprising:
   (i) combining annual and/or perennial plant material with a formic acid mixture comprising formic acid and at least 5% by weight of acetic acid, and treating the plant material at a reaction temperature of between 50° C. and 115° C.; and (ii) separating, at atmospheric pressure, a solid fraction comprising the paper pulp from the formic acid mixture, and from dissolved monomeric and polymeric sugars, lignins and acetic acid resulting from the treated plant material;

wherein the plant material was pre-impregnated at atmospheric pressure and at a temperature lower by at least 30° C. than the reaction temperature.

8. The process according to claim 1, further comprising washing the lignins from step (d) to remove residual sugars and residual acid from the lignins.

9. The process according to claim 8, wherein the sugar content of the washed lignins is less than 1%.

10. The process according to claim 1, wherein the acidic paper pulp extraction liquor is a formic acid and acetic acid based extraction liquor.

11. A process for producing lignins, comprising:
(i) combining annual and/or perennial plant material with a solution comprising formic acid and at least 5% by weight of acetic acid, and treating the combination at a reaction temperature of between 50° C. and 115° C., to extract lignins from the plant material, wherein the plant material was pre-impregnated at atmospheric pressure and at a temperature lower by at least 30° C. than said reaction temperature;

(ii) separating, at atmospheric pressure, a solid fraction comprising paper pulp from the reaction mixture solution of step (i), said separated solution forming an extraction liquor comprising the extracted lignins;

(iii) concentrating the extraction liquor by evaporation to obtain a concentrated liquor comprising dry matter in an amount of between 60% and 70% by weight;

(iv) adding the concentrated liquor to an equal part by weight of water, and mixing to produce a solution mixture;

(v) stirring the solution mixture from step (iv) and adjusting the temperature of the solution mixture to a temperature of between 50° C. and 60° C. to disperse the lignins and to obtain a stable suspension of the lignins in solution; and (vi) filtering the suspension of lignins in solution from step (v) to remove the lignins.

12. The process according to claim 11, further comprising (vii) washing the retained lignins from step (vi) with water.

13. The process according to claim 12, wherein:
during step (vi) the suspension of lignins in solution are filtered at a filtration pressure of 5 bar; and
during step (vii) the retained lignins are washed at a washing pressure of 2.5 bar with water at a temperature of greater than 40° C.

* * * * *